(12) United States Patent
Lehmann-Lintz et al.

(10) Patent No.: US 6,818,644 B1
(45) Date of Patent: Nov. 16, 2004

(54) SUBSTITUTED PIPERAZINE DERIVATIVES, THE PREPARATION THEREOF AND THEIR USE AS MEDICAMENTS

(75) Inventors: Thorsten Lehmann-Lintz, Ochsenhausen (DE); Armin Heckel, Biberach (DE); Leo Thomas, Biberach (DE); Michael Mark, Biberach (DE)

(73) Assignee: Boehringer Ingelheim Pharm GmbH & Co, KG, Ingelheim (DE)

( * ) Notice: Subject to any disclaimer, the term of this patent is extended or adjusted under 35 U.S.C. 154(b) by 36 days.

(21) Appl. No.: 10/089,024

(22) PCT Filed: Sep. 19, 2000

(86) PCT No.: PCT/EP00/09146

§ 371 (c)(1), (2), (4) Date: Jul. 1, 2002

(87) PCT Pub. No.: WO01/21604

PCT Pub. Date: Mar. 29, 2001

(30) Foreign Application Priority Data

Sep. 23, 1999 (DE) .......................... 199 45 594

(51) Int. Cl.$^7$ .................. A61K 31/495; A61K 31/496; C07D 295/112; C07D 401/04; C07D 403/04

(52) U.S. Cl. .......................... 514/252.14; 514/254.02; 514/254.03; 514/253.01; 514/255.03; 514/218; 544/295; 544/360; 544/367; 544/369; 544/379; 544/380; 540/575

(58) Field of Search .................. 544/380, 360, 544/367, 295, 369, 379; 514/253.01, 255.03, 254.03, 252.14, 254.02

(56) References Cited

U.S. PATENT DOCUMENTS 2,838,509 A * 6/1958 Cusic .................. 544/150

FOREIGN PATENT DOCUMENTS

EP 1 180 514 A1 * 2/2002

OTHER PUBLICATIONS

Derwent Abstract for WO 00/61556 (Oct. 19, 2000).*
Ohkura et al. Chemical Abstracts, vol. 133, No. 309907 Abstract for WO 00/61556 (Oct. 19, 2000).*

* cited by examiner

*Primary Examiner*—Emily Bernhardt
(74) *Attorney, Agent, or Firm*—Robert P. Raymond; Anthony P. Bottino; Timothy X. Witkowski

(57) ABSTRACT

The present invention relates to substituted piperazine derivatives of general formula (I)

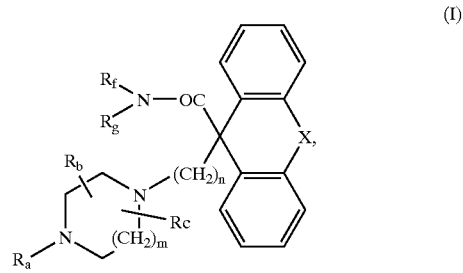

wherein $R_a$, $R_b$, $R_c$, $R_f$, $R_g$ and m, n and X are defined as in claim 1, the isomers and salts thereof, particularly the physiologically acceptable salts thereof, which are valuable inhibitors of the microsomal triglyseride-transfer protein (MTP), medicaments containing these compounds and their use, as well as the preparation thereof.

10 Claims, No Drawings

SUBSTITUTED PIPERAZINE DERIVATIVES, THE PREPARATION THEREOF AND THEIR USE AS MEDICAMENTS

This application claims priority PCT/EP00/09146 and is a national stage case filed under 35 USC 371.

The present invention relates to substituted piperazine derivatives of general formula

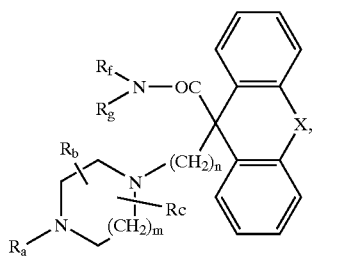

(I)

their isomers, their salts, particularly the physiologically acceptable salts thereof which have valuable pharmacological properties.

The compounds of the above general formula I are valuable inhibitors of the microsomal triglyceride-transfer protein (MTP) and are therefore suitable for lowering the plasma level of the atherogenic lipoproteins.

In the above general formula I n denotes the number 1, 2, 3, 4 or 5, m denotes the number 2 or 3, X denotes a carbon-carbon bond, an oxygen atom, a methylene, ethylene, imino or N-($C_{1-3}$-alkyl)-imino group, $R_a$ denotes a phenyl group or heteroaryl group substituted by the groups $R_1$ and $R_2$, wherein $R_1$ denotes a hydrogen, fluorine, chlorine or bromine atom, a $C_{1-3}$-alkyl group wherein the hydrogen atoms may be wholly or partly replaced by fluorine atoms, a hydroxy group, a $C_{1-4}$-alkoxy group wherein the hydrogen atoms may be wholly or partly replaced by fluorine atoms, a phenoxy, heteroaryloxy, phenyl-$C_{1-3}$-alkoxy, carboxy, $C_{1-3}$-alkoxycarbonyl, aminocarbonyl, $C_{1-3}$-alkylaminocarbonyl, N,N-di-($C_{1-3}$-alkyl)-aminocarbonyl, nitro, amino, $C_{1-3}$-alkylamino, di-($C_{1-3}$-alkyl)-amino, phenyl-$C_{1-3}$-alkyl-amino, N-($C_{1-3}$-alkyl)-phenyl-$C_{1-3}$-alkylamino, $C_{1-3}$-alkylcarbonylamino, N-($C_{1-3}$-alkyl)-$C_{1-3}$-alkylcarbonyl-amino, $C_{1-3}$-alkylsulphonyl-amino or N-($C_{1-3}$-alkyl)-$C_{1-3}$-alkylsulphonylamino group, while the abovementioned phenyl or heteroaryl moieties of the group $R_1$ may be substituted by one to five fluorine, chlorine or bromine atoms, a $C_{1-3}$-alkyl group wherein the hydrogen atoms may be wholly or partly replaced by fluorine atoms, a hydroxy group, or a $C_{1-4}$-alkoxy group wherein the hydrogen atoms may be wholly or partly replaced by fluorine atoms, and $R_2$ denotes a hydrogen, fluorine, chlorine or bromine atom, a $C_{1-3}$-alkyl group wherein the hydrogen atoms may be wholly or partly replaced by fluorine atoms, or a $C_{1-4}$-alkoxy group wherein the hydrogen atoms may be wholly or partly replaced by fluorine atoms, or $R_1$ and $R_2$ together represent a methylenedioxy group, or $R_a$ denotes a monocyclic heteroaryl or phenyl group which is substituted in each case by a phenyl or monocyclic heteroaryl group, while the abovementioned phenyl groups and heteroaryl groups may in each case be substituted by a fluorine, chlorine or bromine atom, a $C_{1-3}$-alkyl group wherein the hydrogen atoms may be wholly or partly replaced by fluorine atoms, by a hydroxy, $C_{1-3}$-alkoxy, carboxy, $C_{1-3}$-alkoxycarbonyl, amino-carbonyl, $C_{1-3}$-alkylaminocarbonyl or N,N-di-($C_{1-3}$-alkyl)-aminocarbonyl group, $R_b$ and $R_c$ independently of one another denote a hydrogen atom or a $C_{1-3}$-alkyl group and $R_f$ and $R_g$, which may be identical or different, denote hydrogen atoms, $C_{1-6}$-alkyl groups wherein the hydrogen atoms may be wholly or partly replaced by fluorine atoms, $C_{3-7}$-cycloalkyl groups, phenyl, heteroaryl, phenyl-$C_{1-3}$-alkyl or heteroaryl-$C_{1-3}$-alkyl groups, while the abovementioned phenyl groups and heteroaryl groups may in each case be substituted by one to three fluorine, chlorine or bromine atoms, by one to three $C_{1-3}$-alkyl groups wherein the hydrogen atoms may be wholly or partly replaced by fluorine atoms, by one to three hydroxy groups, one to three $C_{1-3}$-alkoxy groups wherein the hydrogen atoms may be wholly or partly replaced by fluorine atoms, or by a carboxy, $C_{1-3}$-alkoxycarbonyl, aminocarbonyl, $C_{1-3}$-alkylaminocarbonyl, N,N-di-($C_{1-3}$-alkyl)-aminocarbonyl, N,N-di-($C_{1-3}$-alkyl)-amino, nitro or amino group, or $R_f$ and $R_g$ together with the nitrogen atom between them denote a 3- to 7-membered cycloalkyleneimino group, while the methylene group in the 4 position of a 6- or 7-membered cycloalkyleneimino group may additionally be replaced by an oxygen or sulphur atom, by a sulphinyl, sulphonyl, imino or N-($C_{1-3}$-alkyl)-imino group, while the tricyclic group in the abovementioned general formula I may be mono- or disubstituted by fluorine or chlorine atoms, by methyl or methoxy groups and the substituents may be identical or different.

By the abovementioned heteroaryl groups are meant 6-membered heteroaryl groups containing one, two or three nitrogen atoms, or 5-membered heteroaryl groups which may contain one to four heteroatoms such as, for example, nitrogen, oxygen and sulphur, while hydrogen atoms bound to nitrogen may optionally be replaced by $C_{1-3}$-alkyl groups.

Preferred compounds of the above general formula I are those wherein n denotes the number 3, 4 or 5, m denotes the number 2 or 3, X denotes a carbon-carbon bond, an oxygen atom, a methylene, ethylene, imino or N-($C_{1-3}$-alkyl)-imino group, $R_a$ denotes a phenyl group or heteroaryl group substituted by the groups $R_1$ and $R_2$, wherein $R_1$ denotes a hydrogen, fluorine, chlorine or bromine atom, a $C_{1-3}$-alkyl group wherein the hydrogen atoms may be wholly or partly replaced by fluorine atoms, a hydroxy group, a $C_{1-4}$-alkoxy group wherein the hydrogen atoms may be wholly or partly replaced by fluorine atoms, a phenoxy, heteroaryloxy, phenyl-$C_{1-3}$-alkoxy, carboxy, $C_{1-3}$-alkoxycarbonyl, aminocarbonyl, $C_{1-3}$-alkylaminocarbonyl, N,N-di-($C_{1-3}$-alkyl)-aminocarbonyl, nitro, amino, $C_{1-3}$-alkylamino, di-($C_{1-3}$-alkyl)-amino, phenyl-$C_{1-3}$-alkyl-amino, N-($C_{1-3}$-alkyl)-phenyl-$C_{1-3}$-alkylamino, $C_{1-3}$-alkylcarbonylamino, N-($C_{1-3}$-alkyl)-$C_{1-3}$-alkylcarbonylamino, $C_{1-3}$-alkylsulphonylamino or N-($C_{1-3}$-alkyl)-$C_{1-3}$-alkylsulphonylamino group, while the abovementioned phenyl or heteroaryl moieties of the group $R_1$ may be substituted by one to five fluorine, chlorine or bromine atoms, a $C_{1-3}$-alkyl group wherein the hydrogen atoms may be wholly or partly replaced by fluorine atoms, a hydroxy group, or a $C_{1-4}$-alkoxy group wherein the hydrogen atoms may be wholly or partly replaced by fluorine atoms, and $R_2$ denotes a hydrogen, fluorine, chlorine or bromine atom, a $C_{1-3}$-alkyl group wherein the hydrogen atoms may be wholly or partly replaced by fluorine atoms, or a $C_{1-4}$-alkoxy group wherein the hydrogen atoms may be wholly or partly replaced by fluorine atoms, or $R_1$ and $R_2$ together represent a methylenedioxy group, or $R_a$ denotes a monocyclic heteroaryl or phenyl group which is substituted in each case by a phenyl or monocyclic heteroaryl group, while the abovementioned phenyl groups and heteroaryl groups may in each case be substituted by a fluorine, chlorine or bromine atom, a $C_{1-3}$-alkyl group wherein the hydrogen atoms may be wholly or partly replaced by fluorine atoms, by a hydroxy, or $C_{1-3}$-alkoxy group, $R_b$ and $R_c$ independently of one another denote a hydrogen atom or a $C_{1-3}$-alkyl group and $R_f$ and $R_g$, which may be identical or different, denote hydrogen atoms, $C_{1-6}$-alkyl groups wherein the hydrogen atoms may be wholly or partly replaced by fluorine atoms, $C_{3-7}$-cycloalkyl groups, phenyl, heteroaryl, phenyl-$C_{1-3}$-alkyl or heteroaryl-$C_{1-3}$-alkyl groups, while the abovementioned phenyl groups and heteroaryl groups may in each case be substituted by one to three fluorine, chlorine or bromine atoms, by one to three $C_{1-3}$-alkyl-groups, wherein the-hydrogen-atoms may be wholly or partly replaced by fluorine atoms, by one to three hydroxy groups, one to three $C_{1-3}$-alkoxy groups wherein the hydrogen atoms may be wholly or partly replaced by fluorine atoms, or by a carboxy, $C_{1-3}$-alkoxycarbonyl, aminocarbonyl, $C_{1-3}$-alkylaminocarbonyl, N,N-di-($C_{1-3}$-alkyl)-aminocarbonyl, N,N-di-($C_{1-3}$-alkyl)-amino, nitro or amino group, or $R_f$ and $R_g$ together with the nitrogen atom between them denote a 3- to 7-membered cycloalkyleneimino group, while the methylene group in the 4 position of a 6- or 7-membered cycloalkyleneimino group may additionally be replaced by an oxygen or sulphur atom, by a sulphinyl, sulphonyl, imino or N-($C_{1-3}$-alkyl)-imino group, the isomers and the salts thereof.

Particularly preferred compounds of the above general formula I are those wherein n denotes the number 3, 4 or 5, m denotes the number 2 or 3, X denotes a carbon-carbon bond or an oxygen atom, $R_a$ is as hereinbefore defined, and $R_b$ and $R_c$ independently of one another denote a hydrogen atom or a methyl group and $R_f$ denotes a hydrogen atom, a $C_{1-6}$-alkyl group wherein the hydrogen-atoms may be wholly or partly replaced by fluorine atoms, a $C_{3-7}$-cycloalkyl group, phenyl, heteroaryl, phenyl-$C_{1-3}$-alkyl or heteroaryl-$C_{1-3}$-alkyl group, while the abovementioned phenyl groups and heteroaryl groups may in each case be substituted by one to three fluorine, chlorine or bromine atoms, by one to three $C_{1-3}$-alkyl groups wherein the hydrogen atoms may be wholly or partly replaced by fluorine atoms, by one to three hydroxy groups, one to three $C_{1-3}$-alkoxy groups wherein the hydrogen atoms may be wholly or partly replaced by fluorine atoms, or by a nitro or amino group, and $R_g$ denotes a hydrogen atom, the isomers and the salts thereof.

The following are mentioned as examples of particularly valuable compounds:

(a) 9-[4-(4-biphenyl-3-yl-piperazin-1-yl)-butyl]-9H-fluorene-9-carboxylic acid-(2,2,2-trifluoroethyl)-amide and (b) 9-[4-(4-biphenyl-4-yl-piperazin-1-yl)-butyl]-9H-fluorene-9-carboxylic acid-(2,2,2-trifluoroethyl)-amide, the isomers and the salts thereof.

According to the invention, the new compounds are obtained by methods known from the literature, for example by the following methods:

a. reacting a compound of general formula

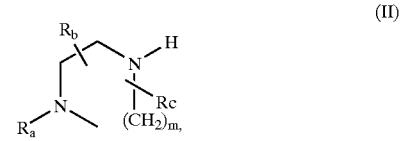

(II)

wherein $R_a$, $R_b$ and $R_c$ are as hereinbefore defined, with a compound of general formula

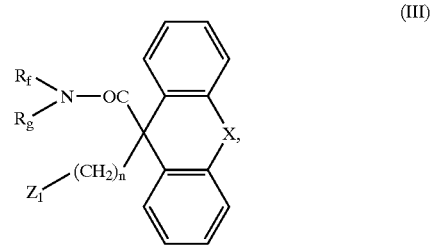

(III)

wherein n, $R_f$, $R_g$ and the tricyclic system are as hereinbefore defined and $Z_1$ denotes a nucleofugic leaving group such as a halogen atom, e.g. a chlorine, bromine or iodine atom.

The reaction is preferably carried out in a solvent such as methylene chloride, acetonitrile, tetrahydrofuran, toluene, acetone/water, dimethylformamide or dimethylsulphoxide, optionally in the presence of a base such as sodium hydride, potassium carbonate, potassium tert-butoxide or N-ethyldiisopropylamine at temperatures between 0 and 100° C., preferably at temperatures between 10 and 60° C.

b. reacting a compound of general formula

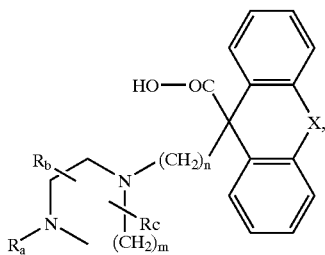

(IV)

wherein
the tricyclic system is as hereinbefore defined, with an amine of general formula

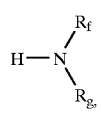

(V)

wherein
$R_f$ and $R_g$ are as hereinbefore defined, or with the reactive derivatives thereof.

The reaction is expediently carried out with a corresponding halide or anhydride of general formula IV in a solvent such as methylene chloride, chloroform, carbon tetrachloride, ether, tetrahydrofuran, dioxane, benzene, toluene, acetonitrile or sulfolane, optionally in the presence of an inorganic or organic base at temperatures between −20 and 200° C., but preferably at temperatures between −10 and 160° C. It may also, however, be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexyl carbodiimide/N-hydroxysuccinimide or 1-hydrbxybenzotriazole, N,N'-carbonyldiimidazole or N,N'-thionyldiimidazole or triphenylphosphine/carbon tetrachloride, at temperatures between −20 and 200° C., but preferably at temperatures between −10and 160° C.

If according to the invention a compound of general formula I is obtained which contains a nitro group, it may be converted by reduction into a corresponding amino compound or
if a compound of general formula I is obtained wherein $R_f$ denotes a hydrogen atom, it may be converted by alkylation into a corresponding compound wherein $R_f$ denotes a $C_{1-3}$-alkyl or phenyl-$C_{1-3}$-alkyl group.

The subsequent reduction of a nitro group is expediently carried out hydrogenolytically, e.g. with hydrogen in the presence of a catalyst such as platinum, palladium/charcoal or Raney nickel in a suitable solvent such as methanol, ethanol, ethyl acetate, tetrahydrofuran, dioxane, dimethylformamide or glacial acetic acid, optionally with the addition of an acid such as hydrochloric acid and at a hydrogen pressure of 1 to 7 bar, but preferably 1 to 5 bar, with metals such as iron, tin or zinc in the presence of an acid such as acetic acid or hydrochloric acid, with salts such as iron(II) sulphate, tin (II) chloride, sodium sulphide, sodium hydrogen sulphite or sodium dithionite, or with hydrazine in the presence of Raney nickel at temperatures between 0 and 100° C., but preferably at temperatures between 20 and 60° C.

The subsequent alkylation is optionally carried out in a solvent or mixture of solvents such as methylene chloride, dimethylformamide, benzene, toluene, chlorobenzene, tetrahydrofuran, benzene/tetrahydrofuran, dioxane, dimethylsulphoxide or sulfolane with an alkylating agent such as a corresponding halide or sulphonic acid ester, e.g. with methyl iodide, ethyl bromide, dimethylsulphate or benzyl chloride, optionally in the presence of a tertiary organic base or in the presence of an inorganic base, expediently at temperatures between 0 and 150° C., preferably at temperatures between 0 and 100° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, tert.butyl-dimethylsilyl, acetyl, benzoyl, methyl, ethyl, tert.butyl, trityl, benzyl or tetrahydropyranyl group,
a protecting group for a carboxyl group may be a trimethylsilyl, methyl, ethyl, tert.butyl, benzyl or tetrahydropyranyl group and
protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C. However, a silyl group may also be cleaved using tetrabutylammonium fluoride as described hereinbefore.

However, a benzyl, methoxybenzyl or benzyloxycarbonyl group is cleaved for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained maybe resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by, the action of suitable agents. Optically active acids in common use are e.g. the D- and L-forms of tartaric acid or dibenzoyltartaric acid, di-o-tolyltartaric acid, malicacid, mandelic acid, camphorsulphonic acid, glutamic acid, aspartic acid or quinic acid. Anoptically active alcohol may be, for example, (+) or (−)-menthol and an optically active acyl group in amides may be, for example, a (+)- or, (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to VI used as starting materials are known from the literature in some cases or may be obtained by methods known from the literature or are described in the Examples.

The compounds of general formula II are obtained, for example, by reacting a compound of general formula

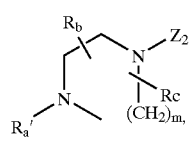 (VI)

wherein $R_b$ and $R_c$ are as hereinbefore defined, $Z_2$ denotes a protecting group for an amino group, e.g. the tert.butoxycarbonyl or benzyloxycarbonyl group, and $R_a'$ denotes, for example, a phenyl or monocyclic heteroaryl group substituted by a bromine or iodine atom, with a, for example, trifluoromethyl-substituted monocyclic aryl or heteroaryl group which is additionally substituted by a boric acid group, in the presence of a catalyst such as palladium acetate, a base such as potassium tert.butoxide and a phase transfer catalyst such as tetrabutylammonium iodide in a solvent such as water, DMF, toluene or mixtures thereof at temperatures of between 20 and 130° C. The protecting group is cleaved by methods known from the literature and leads to a compound of general formula II.

A compound of general formula III is obtained, for example, by reacting a corresponding disubstituted carboxylic acid with an α,ω-dihaloalkane in the presence of a strong base such as lithium diisopropylamide, sodium amide or sodium hydride and subsequently reacting the carboxylic acid with a corresponding amine.

As already mentioned hereinbefore, the compounds of general formula I and the physiologically acceptable salts thereof have valuable pharmacological properties. In particular, they are valuable inhibitors of the microsomal triglyceride-transfer protein (MTP) and are therefore suitable for lowering the plasma levels of the atherogenic lipoproteins.

For example, the compounds according to the invention were investigated for their biological effects as follows:

Inhibitors of MTP were identified by a cell-free MTP activity kit. Solubilised liver microsomes from various species (e.g. rat, pig) could be used as the MTP source. To prepare donor and acceptor vesicles, lipids dissolved in organic solvents were mixed in suitable proportions and applied in a thin layer to the wall of a glass container by blowing the solvent in a nitrogen current. The solution used to prepare donor vesicles contained 400 μM phosphatidylcholine, 75 μM cardiolipin and 10 μM [$^{14}$C]-triolein (68.8 μCi/mg). To prepare acceptor vesicles, a solution of 1.2 mM phosphatidylcholine, 5 μM triolein and 15 μM [$^{3}$H]-dipalmitoylphosphatidylcholine (108 mCi/mg) was used. Vesicles are formed by wetting the dried lipids with test buffer and then subjecting to ultrasound. Vesicle populations of uniform size were obtained by gel filtration of the ultrasonicated lipids. The MTP activity test contains donor vesicles, acceptor vesicles and the MTP source in test buffer. Substances were added from concentrated DMSO-containing stock solutions; the final concentration of DMSO in the test was 0.1%. The reaction was started by the addition of MTP. After a suitable incubation period the transfer process was stopped by the addition of 500 μl of a SOURCE 30Q anion exchanger suspension (Pharmacia Biotech). The mixture was shaken for 5 minutes and the donor vesicles bound to the anion exchanger material were separated off by centrifuging. The radioactivity of [3H] and [14C] found in the supernatant was determined by liquid scintillation measurement and from this the recovery of the acceptor vesicles and the triglyceride transfer rate were calculated.

In view of the abovementioned biological properties the compounds of general formula I and the physiologically acceptable salts thereof are particularly suitable for lowering the plasma concentration of atherogenic apolipoprotein B (apoB)-containing lipoproteins such as chylomicrons and/or very low density lipoproteins (VLDL) as well as the residues thereof such as low density lipoproteins (LDL) and/or lipoprotein(a) (Lp(a)), for treating hyperlipidaemias, for preventing and treating atherosclerosis and the clinical sequela thereof, and for preventing and treating related disorders such as diabetes mellitus, adiposity and pancreatitis, oral administration being preferred.

The daily dose needed to achieve such an effect is between 0.5 and 500 mg, expediently between 1 and 350 mg, but preferably between 5 and 200 mg, in adults.

For this purpose, the compounds of formula I prepared according to the invention, optionally combined with other active substances such as other lipid-lowering agents, for example HMG-CoA-reductase inhibitors, cholesterol biosynthesis inhibitors such as squalene synthase inhibitors and squalene cyclase inhibitors, bile acid-binding resins, fibrates, cholesterol resorption inhibitors, niacin, probucol, CETP inhibitors and ACAT inhibitors may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

EXAMPLE 1

9-[4-(4-phenyl-piperazin-1-yl)-butyl]-9H-fluorene-9-carboxylic acid-(2,2,2-trifluoro-ethyl)-amide a. 9-(4-bromo-butyl)-9H-fluorene-9-carboxylic acid 89 ml (0.11 mol) of a 1.6 M butyllithium solution in hexane are added dropwise at 0° C. to a solution of 21 g (0.1 mol) of 9-fluorenecarboxylic acid in 700 ml tetrahydrofuran under nitrogen and stirred for one hour. Then, still at 0° C., 13.13 ml (0.11 mol) of dibromobutane are added and the solution is stirred for 30 hours at ambient temperature. After this time, 50 ml of water are added and the mixture is stirred for 30 minutes. The solution is evaporated down, combined with water and extracted with 250 ml of diethyl ether. The aqueous phase is acidified with 150 ml of 1N hydrochloric acid and extracted three times with 250 ml of dichloromethane. The combined organic phases are dried over sodium sulphate and the solvent is removed.

Yield: 18.5 g (53.6% of theoretical),

Melting point: 123° C.

b. 9-(4-bromo-butyl)-9H-fluorene-9-carboxylic acid chloride 23 g (0.067 mol) of 9-(4-bromo-butyl)-9H-fluorene-9-carboxylic acid are dissolved in 40 ml dichloromethane and combined with three drops of dimethylformamide and 6.96 ml (0.081 mol) of oxalyl chloride, dissolved in 10 ml dichloromethane, under nitrogen at 0° C. The mixture is stirred for 3 hours at ambient temperature. Then the solvent is removed and the crude product is further reacted without any more purification.

Yield: 24 g (99% of theoretical)

c. 9-(4-bromo-butyl)-9H-fluorene-9-carboxylic acid-(2,2,2-trifluoroethyl)-amide 23 g (0.063 mol) of 9-(4-bromo-butyl)-9H-fluorene-9-carboxylic acid chloride are added dropwise at 0° C. under nitrogen to a solution of 9.35 g (0.069 mol) of 2,2,2-trifluoroethylamine-hydrochloride and 26 ml (0.188 mol) of triethylamine in 550 ml of dichloromethane and stirred for 2 hours at ambient temperature. The reaction mixture is extracted twice with water, 1N hydrochloric acid and sodium hydrogen carbonate solution. The organic phase is dried over sodium sulphate and the solvent is distilled off. Purification is by column chromatography on silica gel (eluant: cyclohexane/ethyl acetate=8:1).

Yield: 15.8 g (58.6% of theoretical),

Melting point: 172° C.

d. 9-[4-(4-phenyl-piperazin-1-yl)-butyl)-9H-fluorene-9-carboxylic acid-(2,2,2-trifluoro-ethyl)-amide A suspension of 0.4 g (0.93 mmol) of 9-(4-bromo-butyl)-9H-fluorene-9-carboxylic acid-(2,2,2-trifluoroethyl)-amide, 0.153 ml (1 mmol) of 1-phenylpiperazine, 0.8 g of potassium carbonate and 1 ml water in 30 ml dimethylformamide is stirred for 10 hours at 80° C. The reaction mixture is then poured onto water, extracted with ethyl acetate and the organic phase is dried over sodium sulphate. Purification is by column chromatography on silica gel (eluant: dichloromethane/methanol=15:1).

Yield: 0.1 g (19.7% of theoretical),

Melting point: 127–128° C.

EXAMPLE 2

9-[4-(4-biphenyl-3-yl-piperazin-1-yl)-butyl]-9H-fluorene-9-carboxylic acid-(2,2,2-trifluoroethyl)-amide a. 1-biphenyl-3-yl-piperazin-dihydrochloride A suspension of 1 g (4.29 mmol) of 3-bromobiphenyl, 2.2 g (25.54 mmol) of piperazine and 2.499 g (26 mmol) of sodium tert.butoxide in 40 ml toluene is heated to 80 [sic] under nitrogen. Then 0.01 g (0.011 mmol) of tris (dibenzylidene-acetone)dipalladium(0) and 0.02 g (0.032 mmol) of BINAP are added, the mixture is heated to 86 [sic] for 7 hours and stirred for 14 hours at ambient temperature. Water and ethyl acetate are added in succession, theorganic phase is separated off, dried over sodium sulphate and evaporated down. The residue is combined with an ethereal hydrochloric acid solution and diisopropyl ether and the precipitate formed is filtered off.

Yield: 1.05 g (78.6% of theoretical),

Melting point: 219–221° C.

$C_{16}H_{18}N_2$ (M=238.34).

Calc.: molpeak $(M+H)^+$: 239. Found: molpeak $(M+H)^+$: 239.

b. 9-[4-(4-biphenyl-3-yl-piperazin-1-yl)-butyl]-9H-fluorene-9-carboxylic acid-(2,2,2-trifluoroethyl)-amide A suspension of 0.2 g (0.643 mmol) of 1-biphenyl-3-yl-piperazine-dihydrochloride, 0.256 g (0.6 mmol) of 9-(4-bromo-butyl)-9H-fluorene-9-carboxylic acid-(2,2,2-trifluoroethyl)-amide and 0.1 g potassium carbonate in 20 ml of acetonitrile and 0.1 ml of water is stirred for 24 hours at 60° C. The reaction mixture is poured onto water, extracted with ethyl acetate and dried over sodium sulphate. Purification is by column chromatography on silica gel (eluant: dichloromethane/ethanol=30:1).

Yield: 0.2 g (53.3% of theoretical), $C_{36}H_{36}F_3N_3O$ (M=583.70).

Calc.: molpeak $(M)^+$: 583. Found: molpeak $(M)^+$: 583.

EXAMPLE 3

9-[4-(4-biphenyl-4-yl-piperazin-1-yl)-butyl]-9H-fluorene-9-carboxylic acid-(2,2,2-trifluoroethyl)-amide a. 1-Benzyl-4-biphenyl-4-yl-piperazine 1.6 ml (0.05 mol) of butyllithium solution in n-hexane is added dropwise to a solution of 8.81 g (0.05 mol) of 1-benzylpiperazine in 50 ml of anhydrous THF under argon at 0° C. and stirred for one hour. Then 9.21 g (0.05 mol) of 4-methoxybiphenyl are added and the reaction mixture is refluxed for 12 hours. The solvent is then evaporated off, the residue is combined with 150 ml of 2 N hydrochloric acid followed by diethyl ether and the precipitate formed is filtered off. The precipitate is washed with diethyl ether, suspended in 20% sodium carbonate solution and extracted several times with dichloromethane. After drying over magnesium sulphate the solvent is removed and the residue is washed with ethyl acetate and diethyl ether.

Yield: 12.5 g (85% of theoretical).

Melting point: 146–148° C.

b. 1-biphenyl-4-yl-piperazine

A suspension of 12.45 g (0.037 mol) of 1-benzyl-4-biphenyl-4-yl-piperazine and 4 g of palladium hydroxide in 360 ml of methanol is stirred for 6 hours at ambient temperature in a Parr apparatus under a hydrogen pressure of 50 psi. The catalyst is separated off and the filtrate is evaporated down.

Yield: 8.64 g (95.6% of theoretical),

Melting point: 134–138° C.

c. 9-[4-(4-biphenyl-4-yl-piperazin-1-yl)-butyl]-9H-fluorene-9-carboxylic acid-(2,2,2-trifluoroethyl)-amide A solution of 0.4 g (1.678 mmol) of 1-biphenyl-4-yl-piperazine, 0.682 g (1.6 mmol) of 9-(4-bromo-butyl)-9H-fluorene-9-carboxylic acid-(2,2,2-trifluoroethyl)-amide and 0.223 ml (1.6 mmol) of triethylamine in 20 ml acetonitrile is stirred for 14 hours at 60° C. and then diluted with water. It is extracted with ethyl acetate and the organic phase is dried over sodium sulphate. Purification is by column chromatography on silica gel (eluant: dichloromethane/ethanol=40:1).

Yield: 0.29 g (29.6% of theoretical),

Melting point: 209-211° C.

$C_{36}H_{36}F_3N_3O$ (M=583.70).

Calc.: molpeak (M)$^+$: 583. Found: molpeak (M)$^+$: 583.

EXAMPLE 4

9-{4-[4-(4-Chloro-phenyl)-piperazin-1-yl]-butyl}-9H-fluorene-9-carboxylic acid-(2,2,2-trifluoroethyl)-amide Prepared analogously to Example 2 b from 1-(4-chlorophenyl)-piperazine dihydrochloride and 9-(4-bromo-butyl)-9H-fluorene-9-carboxylic acid-(2,2,2-trifluoroethyl)-amide.

Yield: 0.2 g (54.3% of theoretical),

Melting point: 166° C.

$C_{30}H_{31}ClF_3N_3O$ (M=542.049).

Calc.: molpeak (M)$^+$: 541/543. Found: molpeak (M)$^+$: 541/543.

EXAMPLE 5

9-{4-[4-(3-Chloro-phenyl)-piperazin-1-yl]-butyl}-9H-fluorene-9-carboxylic acid-(2,2,2-trifluoroethyl)-amide Prepared analogously to Example 2 b from 1-(3-chlorophenyl)-piperazine dihydrochloride and 9-(4-bromo-butyl)-9H-fluorene-9-carboxylic acid-(2,2,2-trifluoroethyl)-amide.

Yield: 0.09 g (16.5% of theoretical),

Melting point: 122° C.

$C_{30}H_{31}ClF_3N_3O$ (M=542.049).

Calc.: molpeak (M+H)$^+$: 542/544. Found: molpeak (M+H)$^+$: 542/544.

EXAMPLE 6

9-{4-[4-(4-Benzyloxy-phenyl)-piperazin-1-yl]-butyl}-9H-fluorene-9-carboxylic acid-(2,2,2-trifluoroethyl)-amide Prepared analogously to Example 2 b from 1-(4-benzyloxy-phenyl)-piperazine hydrochloride and 9-(4-bromo-butyl)-9H-fluorene-9-carboxylic acid-(2,2,2-trifluoroethyl)-amide.

Yield: 0.21 g (48.6% of theoretical),

Melting point: 180° C.

$C_{37}H_{38}F_3N_3O_2$ (M=613.73).

Calc.: molpeak (M+H)$^+$: 614. Found: molpeak (M+H)$^+$: 614.

EXAMPLE 7

9-{4-[4-(4-Trifluoromethyl-phenyl)-piperazin-1-yl]-butyl}-9H-fluorene-9-carboxylic acid-(2,2,2-trifluoroethyl)-amide Prepared analogously to Example 2 b from 1-(4-trifluoromethyl-phenyl)-piperazine and 9-(4-bromo-butyl)-9H-fluorene-9-carboxylic acid-(2,2,2-trifluoroethyl)-amide.

Yield: 0.23 g (48.7% of theoretical).

Melting point: 176° C.

$C_{31}H_{31}F_6N_3O$ (M=575.60)

Calc.: molpeak (M+H)$^+$: 576. Found: molpeak (M+H)$^+$: 576.

EXAMPLE 8

9-{4-[4-(3-trifluoromethyl-phenyl)-piperazin-1-yl]-butyl}-9H-fluorene-9-carboxylic acid-(2,2,2-trifluoroethyl)-amide Prepared analogously to Example 2 b from 1-(3-trifluoromethyl-phenyl)-piperazine and 9-(4-bromo-butyl)-9H-fluorene-9-carboxylic acid-(2,2,2-trifluoroethyl)-amide.

Yield: 0.16 g (33.9% of theoretical), $C_{31}H_{31}F_6N_3O$ (M=575.60).

Calc.: molpeak (M+H)$^+$: 576. Found: molpeak (M+H)$^+$: 576.

EXAMPLE 9

9-{4-[4-(4-Fluorophenyl)-piperazin-1-yl]-butyl}-9H-fluorene-9-carboxylic acid-(2,2,2-trifluoroethyl)-amide Prepared analogously to Example 2 b from 1-(4-fluorophenyl)-piperazine and 9-(4-bromo-butyl)-9H-fluorene-9-carboxylic acid-(2,2,2-trifluoroethyl)-amide.

Yield: 0.1 g (23.2% of theoretical).

Melting point: 116–117° C.

$C_{30}H_{31}F_4N_3O$ (M=525.59).

Calc.: molpeak (M+H)$^+$: 526. Found: molpeak (M+H)$^+$: 526.

EXAMPLE 10

9-{4-[4-(4-Chloro-3-trifluoromethyl-phenyl)-piperazin-1-yl]-butyl}-9H-fluorene-9-carboxylic acid-(2,2,2-trifluoroethyl)-amide Prepared analogously to Example 2 b from 1-(4-chloro-3-trifluoromethyl-phenyl)-piperazine and 9-(4-bromo-butyl)-9H-fluorene-9-carboxylic acid-(2,2,2-trifluoroethyl)-amide.

Yield: 0.13 g (26% of theoretical).

Melting point: 96° C.

$C_{31}H_{30}ClF_6N_3O$ (M=610.04).

Calc.: molpeak (M+H)$^+$: 608/610. Found: molpeak (M+H)$^+$: 608/610.

EXAMPLE 11

9-{4-[4-(4-methyl-phenyl)-3-methyl-piperazin-1-yl]-butyl}-9H-fluorene-9-carboxylic acid-(2,2,2-trifluoroethyl)-amide Prepared analogously to Example 2 b from 1-(4-methyl-phenyl)-3-methyl-piperazine and 9-(4-bromo-butyl)-9H-fluorene-9-carboxylic acid-(2,2,2-trifluoroethyl)-amide.

Yield: 0.17 g (38.7% of theoretical).

$C_{32}H_{36}F_3N_3O$ (M=535.65).

Calc.: molpeak $(M)^+$: 535. Found: molpeak $(M)^+$: 535.

EXAMPLE 12

9-{4-[4-(3,4-dichlorophenyl)-piperazin-1-yl]-butyl}-9H-fluorene-9-carboxylic acid-(2,2,2-trifluoroethyl)-amide Prepared analogously to Example 2 b from 1-(3,4-dichlorophenyl)-piperazine and 9-(4-bromo-butyl)-9H-fluorene-9-carboxylic acid-(2,2,2-trifluoroethyl)-amide.

Yield: 0.15 g (31.7% of theoretical).

Melting point: 122° C.

$C_{30}H_{30}Cl_2F_3N_3O$ (M=576.49).

Calc.: molpeak $(M)^+$: 575/577/579. Found: molpeak $(M)^+$: 575/577/579.

EXAMPLE 13

9-{4-[4-(4-methoxy-phenyl)-piperazin-1-yl]-butyl}-9H-fluorene-9-carboxylic acid-(2,2,2-trifluoroethyl)-amide Prepared analogously to Example 2 b from 1-(4-methoxy-phenyl)-piperazine and 9-(4-bromo-butyl)-9H-fluorene-9-carboxylic acid-(2,2,2-trifluoroethyl)-amide.

Yield: 0.2 g (52.8% of theoretical).

Melting point: 120° C.

$C_{31}H_{34}F_3N_3O_2$ (M=537.63).

Calc.: molpeak $(M+H)^+$: 538. Found: molpeak $(M+H)^+$: 538.

EXAMPLE 14

9-{4-[4-(2-methoxy-phenyl)-piperazin-1-yl]-butyl}-9H-fluorene-9-carboxylic acid-(2,2,2-trifluoroethyl)-amide Prepared analogously to Example 2 b from 1-(2-methoxy-phenyl)-piperazine and 9-(4-bromo-butyl)-9H-fluorene-9-carboxylic acid-(2,2,2-trifluoroethyl)-amide.

Yield: 0.1 g (18.6% of theoretical).

$C_{31}H_{34}F_3N_3O_2$ (M=537.63).

Calc.: molpeak $(M+H)^+$: 538. Found: molpeak $(M+H)^+$: 538.

EXAMPLE 15

9-{4-[4-(2,4-Dimethoxy-phenyl)-piperazin-1-yl]-butyl}-9H-fluorene-9-carboxylic acid-(2,2,2-trifluoroethyl)-amide Prepared analogously to Example 2 b from 1-(2,4-dimethoxy-phenyl)-piperazine and 9-(4-bromo-butyl)-9H-fluorene-9-carboxylic acid-(2,2,2-trifluoroethyl)-amide.

Yield: 0.15 g (37.5% of theoretical).

$C_{32}H_{36}F_3N_3O_3$ (M=567.65).

Calc.: molpeak $(M+H)^+$: 568. Found: molpeak $(M+H)^+$: 568.

EXAMPLE 16

9-{4-[4-(5-Chloro-2-methoxy-phenyl)-piperazin-1-yl]-butyl}-9H-fluorene-9-carboxylic acid-(2,2,2-trifluoroethyl)-amide Prepared analogously to Example 2 b from 1-(5-chloro-2-methoxy-phenyl)-piperazine hydrochloride and 9-(4-bromo-butyl)-9H-fluorene-9-carboxylic acid-(2,2,2-trifluoroethyl)-amide.

Yield: 0.11 g (27.3% of theoretical).

$C_{31}H_{33}ClF_3N_3O_2$ (M=572.07).

Calc.: molpeak $(M+H)^+$: 572/574. Found: molpeak $(M+H)^+$: 572/574.

EXAMPLE 17

9-{4-[4-(4-nitro-phenyl)-piperazin-1-yl]-butyl}-9H-fluorene-9-carboxylic acid-(2,2,2-trifluoroethyl)-amide Prepared analogously to Example 2 b from 1-(4-nitro-phenyl)-piperazine and 9-(4-bromo-butyl)-9H-fluorene-9-carboxylic acid-(2,2,2-trifluoroethyl)-amide.

Yield: 0.35 g (38.6% of theoretical).

Melting point: 146° C.

$C_{30}H_{31}F_3N_4O_3$ (M=552.60).

Calc.: molpeak $(M)^+$: 552. Found: molpeak $(M)^+$: 552.

EXAMPLE 18

9-{4-[4-(4-amino-phenyl)-piperazin-1-yl]-butyl}-9H-fluorene-9-carboxylic acid-(2,2,2-trifluoroethyl)-amide hydrochloride A solution of 0.25 g (0.45 mmol) of 9-{4-[4-(4-nitro-phenyl)-piperazin-1-yl]-butyl}-9H-fluorene-9-carboxylic acid-(2,2,2-trifluoroethyl)-amide in a mixture of 20 ml of ethyl acetate and 10 ml of methanol is hydrogenated in the presence of 0.1 g of palladium on charcoal. Then the catalyst is filtered off, the solvent is distilled off and the residue is dissolved in ethanol. After the addition of ethanolic hydrochloric acid solution the solvent is distilled off.

Yield: 0.15 g (59.4% of theoretical).

Melting point: >270° C.

$C_{30}H_{33}F_3N_4O$ X HCl (M=559.08).

Calc.: molpeak $(M+H)^+$: 523. Found: molpeak $(M+H)^+$: 523.

EXAMPLE 19

9-{4-[4-(2-methyl-phenyl)-piperazin-1-yl]-butyl}-9H-fluorene-9-carboxylic acid-(2,2,2-trifluoroethyl)-amide Prepared analogously to Example 2 b from 1-(2-methyl-phenyl)-piperazine and 9-(4-bromo-butyl)-9H-fluorene-9-carboxylic acid-(2,2,2-trifluoroethyl)-amide.

Yield: 0.21 g (57.2% of theoretical), $C_{31}H_{34}F_3N_3O$ (M=521.63).

Calc.: molpeak $(M+H)^+$: 522. Found: molpeak $(M+H)^+$: 522.

EXAMPLE 20

9-{4-[4-Pyridin-2-yl-piperazin-1-yl]-butyl}-9H-fluorene-9-carboxylic acid-(2,2,2-trifluoroethyl)-amide Prepared analogously to Example 2 b from 1-pyridin-2-yl-piperazine and 9-(4-bromo-butyl)-9H-fluorene-9-carboxylic acid-(2,2,2-trifluoroethyl)-amide.

Yield: 0.15 g (35.9% of theoretical).

Melting point: 123° C.

$C_{29}H_{31}F_3N_4O$ (M=508.59).

Calc.: molpeak $(M+H)^+$: 509. Found: molpeak $(M+H)^+$: 509.

EXAMPLE 21

9-{4-[4-(6-metboxy-pyridin-2-yl)-piperazin-l-yl]-butyl}-9H-fluorene-9-carboxylic acid-(2,2,2-trifluoroethyl)-amide Prepared analogously to Example 2 b from 1-(6-methoxy-pyridin-2-yl)-piperazine and 9-(4-bromo-butyl)-9H-fluorene-9-carboxylic acid-(2,2,2-trifluoroethyl)-amide.

Yield: 0.38 g (60.1% of theoretical).
Melting point: 131° C.
$C_{30}H_{33}F_3N_4O_2$ (M=538.61).
Calc.: molpeak (M-H): 537. Found: molpeak (M-H); 537.

EXAMPLE 22

9-{4-[4-(6-methoxy-pyridin-2-yl)-piperazin-1-yl]-butyl}-9H-fluorene-9-carboxylic acid-4-fluorobenzyl-amide Prepared analogously to Example 2 b from 1-(6-methoxy-pyridin-2-yl)-piperazine and 9-(4-bromo-butyl)-9H-fluorene-9-carboxylic acid-4-fluorobenzyl-amide.

Yield: 0.05 g (10% of theoretical).
$C_{35}H_{37}FN_4O_2$ (M=564.70).
Calc.: molpeak (M-H): 563. Found: molpeak (M-H): 563.

EXAMPLE 23

9-{4-[4-(6-metboxy-pyridin-2-yl)-piperazin-1-yl]-butyl}-9H-fluorene-9-carboxylic acid-4-methoxybenzyl-amide Prepared analogously to Example 2 b from 1-(6-methoxy-pyridin-2-yl)-piperazine and 9-(4-bromo-butyl)-9H-fluorene-9-carboxylic acid-4-methoxybenzyl-amide.

Yield: 0.02 g (8% of theoretical).
$C_{36}H_{40}N_4O_3$ (M=576.74).
Calc.: molpeak (M+H)$^+$: 577. Found: molpeak (M+H)$^+$: 577.

EXAMPLE 24

9-{4-[4-(6-ethoxy-pyridin-2-yl)-piperazin-1-yl]-butyl}-9H-fluorene-9-carboxylic acid-(2,2,2-trifluoroethyl)-amide Prepared analogously to Example 2 b from 1-(6-ethoxy-pyridin-2-yl)-piperazine and 9-(4-bromo-butyl)-9H-fluorene-9-carboxylic acid-(2,2,2-trifluoroethyl)-amide.

Yield: 0.03 g (8.5% of theoretical).
$C_{31}H_{35}F_3N_4O_2$ (M=552.64).
Calc.: molpeak.(M+H)$^+$: 553. Found: molpeak (M+H)$^+$: 553.

EXAMPLE 25

9-{4-[4-(6-methyl-pyridin-2-yl)-piperazin-1-yl]-butyl}-9H-fluorene-9-carboxylic acid-(2,2,2-trifluoroethyl)-amide Prepared analogously to Example 2 b from 1-(6-methyl-pyridin-2-yl)-piperazine and 9-(4-bromo-butyl)-9H-fluorene-9-carboxylic acid-(2,2,2-trifluoroethyl)-amide.

Yield: 0.04 g (7.7% of theoretical).
Melting point: 85–87° C.
$C_{30}H_{33}F_3N_4O$ (M=522.61).
Calc.: molpeak (M+H)$^+$: 523. Found: molpeak (M+H)$^+$: 523.

EXAMPLE 26

9-{4-[4-(6-methyl-pyridin-2-yl)-piperazin-1-yl]-butyl}-9H-fluorene-9-carboxylic acid-4-fluorobenzyl-amide Prepared analogously to Example 2 b from 1-(6-methyl-pyridin-2-yl)-piperazine and 9-(4-bromo-butyl)-9H-fluorene-9-carboxylic acid-4-fluorobenzyl-amide.

Yield: 0.16 g (44% of theoretical).
Melting point: 96–97° C.
$C_{35}H_{37}FN_4O$ (M=548.71).
Calc.: molpeak (M+H)$^+$: 549. Found: molpeak (M+H)$^+$: 549.

EXAMPLE 27

9-{4-[4-(5-trifluoromethyl-pyridin-2-yl)-piperazin-1-yl]-butyl}-9H-fluorene-9-carboxylic acid-(2,2,2-trifluoroethyl)-amide Prepared analogously to Example 2 b from 1-(5-trifluoromethyl-pyridin-2-yl)-piperazine and 9-(4-bromo-butyl)-9H-fluorene-9-carboxylic acid-(2,2,2-trifluoroethyl)-amide.

Yield: 0.19 g (33% of theoretical).
Melting point: 147–149° C.
$C_{30}H_{30}F_6N_4O$ (M=576.59).
Calc.: molpeak (M+H)$^+$: 577. Found: molpeak (M+H)$^+$: 577.

EXAMPLE 28

9-{4-[4-(6-phenyl-pyridin-2-yl)-piperazin-1-yl]-butyl}-9H-fluorene-9-carboxylic acid-(2,2,2-trifluoroethyl)-amide a. tert.butyl 4-(6-bromo-pyridin-2-yl)-piperazine-1-carboxylate A solution of 4 g (16.88 mmol) of 2,6-dibromopyridine, 3.14 g (16.88 mmol) of tert.butyl piperazine-1-carboxylate and 5.89 ml (33.77 mmol) of N,N-diisopropylethylamine in 30 ml of n-butanol is refluxed for eight hours. The solvent is then distilled off. Purification is by column chromatography on silica gel (eluant: cyclohexane/ethyl acetate=2:1).

Yield: 2.2 g (38.1% of theoretical).
Melting point: 95° C.
$C_{30}H_{30}F_6N_4O$ (M=576.59).
Calc.: molpeak (M+H)$^+$: 577. Found: molpeak (M+H)$^+$: 577.

b. tert.butyl 4-(6-phenyl-pyridin-2-yl)-piperazine-1-carboxylate

A mixture of 2 g (5.84 mmol) of tert.butyl 4-(6-bromo-pyridin-2-yl)-piperazine-1-carboxylate, 0.75 g (6.15 mmol) of phenylboric acid, 2.66 g (17.52 mmol) of caesium fluoride, 0.045 g (0.15 mmol) of 2-(di-t-butylphosphino)-biphenyl and 0.013 g (0.06 mmol) of palladium acetate in 20 ml of dioxane is stirred for six hours at 50° C. under nitrogen. Then it is diluted with water and the reaction mixture is extracted with ethyl acetate. The organic phase is separated off and dried over sodium sulphate. Purification is by column chromatography on silica gel (eluant: cyclohexane/ethyl acetate=4:1).

Yield: 0.7 g (35.3% of theoretical).
$C_{20}H_{25}N_3O_2$ (M=339.44).
Calc.: molpeak (M+Na)$^+$: 362. Found: molpeak (M+Na)$^+$: 362.

b. [sic] 1-(6-phenyl-pyridin-2-yl)-piperazine

A solution of 0.7 g (2.06 mmol) of tert.butyl 4-(6-phenyl-pyridin-2-yl)-piperazine-1-carboxylate and 3 ml of trifluoroacetic acid in 30 ml of dichloromethane is stirred for three hours at ambient temperature. The solvent is then distilled off, the residue is combined with water and made basic with sodium hydroxide solution. It is then extracted with dichloromethane and the organic phase is separated off and dried over sodium sulphate.

Yield: 0.4 g (81.1% of theoretical).
$C_{15}H_{17}N_3$ (M=239.32).
Calc.: molpeak $(M+H)^+$: 240. Found: molpeak $(M+H)^+$: 240.

d. 9-{4-[4-(6-phenyl-pyridin-2-yl)-piperazin-1-yl]-butyl}-9H-fluorene-9-carboxylic acid-(2,2,2-trifluoroethyl)-amide Prepared analogously to Example 2 b from 1-(6-phenyl-pyridin-2-yl)-piperazine and 9-(4-bromo-butyl)-9H-fluorene-9-carboxylic acid-(2,2,2-trifluoroethyl)-amide.

Yield: 0.05 g (17.1% of theoretical).
Melting point: 63° C.
$C_{35}H_{35}F_3N_4O$ (M=584.69).
Calc.: molpeak $(M+H)^+$: 585. Found: molpeak $(M+H)^+$: 585.

EXAMPLE 29

9-{4-[4-(4-phenyl-pyridin-2-yl)-piperazin-1-yl]-butyl}-9H-fluorene-9-carboxylic acid-(2,2,2-trifluoroethyl)-amide Prepared analogously to Example 2 b from 1-(4-phenyl-pyridin-2-yl)-piperazine and 9-(4-bromo-butyl)-9H-fluorene-9-carboxylic acid-(2,2,2-trifluoroethyl)-amide.

Yield: 0.11 g (26.7% of theoretical).
Melting point: 59° C.
$C_{35}H_{35}F_3N_4O$ (M=584.69).
Calc.: molpeak $(M+H)^+$: 585. Found: molpeak $(M+H)^+$: 585.

EXAMPLE 30

9-{4-[4-(6-phenoxy-pyridin-2-yl)-piperazin-1-yl]-butyl}-9H-fluorene-9-carboxylic acid-(2,2i2-trifluoroethyl)-amide a. 2-Chloro-6-phenoxy-pyridine A reaction mixture consisting of 1.48 g (10 mmol) of 2,6-dichloropyridine, 6 g (63.75 mmol) of phenol and 2.4 g (60 mmol) of sodium hydroxide in 10 ml of water is heated to 140° C. for 24 hours in a bomb. After cooling the reaction mixture is made strongly alkaline with sodium hydroxide solution and extracted with dichloromethane. The organic phase is separated off and dried over sodium sulphate. Purification is by column chromatography on silica gel (eluant: cyclohexane/ethyl acetate=3:1).

Yield: 0.3 g (14.6% of theoretical).
$C_{11}H_8ClNO$ (M=205.64).
Calc.: molpeak $(M+H)^+$: 205/207. Found: molpeak $(M+H)^+$: 205/207.

b. 9-{4-[4-(6-phenoxy-pyridin-2-yl)-piperazin-1-yl]-butyl}-9H-fluorene-9-carboxylic acid-(2,2,2-trifluoroethyl)-amide Prepared analogously to Example 2 b from 2-chloro-6-phenoxy-pyridine and 9-(4-bromo-butyl)-9H-fluorene-9-carboxylic acid-(2,2,2-trifluoroethyl)-amide.

Yield: 0.045 g (15.4% of theoretical).
$C_{35}H_{35}F_3N_4O_2$ (M=600.69).
Calc.: molpeak $(M+H)^+$: 601. Found: molpeak $(M+H)^+$: 601.

EXAMPLE 31

9-(4-{4-[6-(4-Chloro-phenoxy)-pyridin-2-yl]-piperazin-1-yl}-butyl)-9H-fluorene-9-carboxylic acid-(2,2,2-trifluoroethyl)-amide Prepared analogously to Example 2 b from 1-[6-(4-chloro-phenoxy)-pyridin-2-yl]-piperazine and 9-(4-bromo-butyl)-9H-fluorene-9-carboxylic acid-(2,2,2-trifluoroethyl)-amide.

Yield: 0.04 g (15.1% of theoretical).
$C_{35}H_{34}ClF_3N_4O_2$ (M=635.13).
Calc.: molpeak $(M+H)^+$: 635/637. Found: molpeak $(M+H)^+$: 635/637.

EXAMPLE 32

9-(4-{4-[6-(3-Chloro-phenoxy)-pyridin-2-yl]-piperazin-1-yl}-butyl)-9H-fluorene-9-carboxylic acid-(2,2,2-trifluoroethyl)-amide Prepared analogously to Example 2 b from 1-[6-(3-chloro-phenoxy)-pyridin-2-yl]-piperazine and 9-(4-bromo-butyl)-9H-fluorene-9-carboxylic acid-(2,2,2-trifluoroethyl)-amide.

Yield: 0.04 g (15.1% of theoretical).
$C_{35}H_{34}ClF_3N_4O_2$ (M=635.13).
Calc.: molpeak $(M+H)^+$: 635/637. Found: molpeak $(M+H)^+$: 635/637.

EXAMPLE 33

9-(4-{4-[6-(2-Chloro-phenoxy)-pyridin-2-yl]-piperazin-1-yl}-butyl)-9H-fluorene-9-carboxylic acid-(2,2,2-trifluoroethyl)-amide Prepared analogously to Example 2 b from 1-[6-(2-chloro-phenoxy)-pyridin-2-yl]-piperazine and 9-(4-bromo-butyl)-9H-fluorene-9-carboxylic acid-(2,2,2-trifluoroethyl)-amide.

Yield: 0.06 g (22.7% of theoretical).
$C_{35}H_{34}ClF_3N_4O_2$ (M=635.13).
Calc.: molpeak $(M)^+$: 634/636. Found: molpeak $(M)^+$: 634/636.

EXAMPLE 34

9-(4-{4-[6-(4-methoxy-phenoxy)-pyridin-2-yl]-piperazin-1-yl}-butyl)-9H-fluorene-9-carboxylic acid-(2,2,2-trifluoroethyl)-amide Prepared analogously to Example 2 b from 1-[6-(4-methoxy-phenoxy)-pyridin-2-yl]-piperazine and 9-(4-bromo-butyl)-9H-fluorene-9-carboxylic acid-(2,2,2-trifluoroethyl)-amide.

Yield: 0.03 g (11.2% of theoretical).
$C_{36}H_{37}F_3N_4O_3$ (M=630.71).
Calc.: molpeak $(M+H)^+$: 631. Found: molpeak $(M+H)^+$: 631.

EXAMPLE 35

9-{4-[4-(6-methoxy-pyridin-2-yl)-piperazin-1-yl]-butyl}-9H-xanthene-9-carboxylic acid-(2,2,2-trifluoroethyl)-amide Prepared analogously to Example 2 b from 1-(6-methoxy-pyridin-2-yl)-piperazine and 9-(4-bromo-butyl)-9H-xanthene-9-carboxylic acid-(2,2,2-trifluoroethyl)-amide.

Yield: 0.17 g (45.2% of theoretical).
Melting point: 122° C.
$C_{30}H_{33}F_3N_4O_3$ (M=554.61).
Calc.: molpeak $(M+H)^+$: 555. Found: molpeak $(M+H)^+$: 555.

EXAMPLE 36

9-{4-[4-(6-methoxy-pyridin-2-yl)-2,6-dimethyl-piperazin-1-yl]-butyl}-9H-fluorene-9-carboxylic acid-(2,2,2-trifluoroethyl)-amide Prepared analogously to Example 2 b from 1-(6-methoxy-pyridin-2-yl)-3,5-dimethyl-piperazine and 9-(4-bromo-butyl)-9H-fluorene-9-carboxylic acid-(2,2,2-trifluoroethyl)-amide.

Yield: 0.07 g (13.2 % of theoretical).

Melting point: 122° C.

$C_{32}H_{37}F_3N_4O_2$ (M=566.67).

Calc.: molpeak $(M+H)^+$: 567. Found: molpeak $(M+H)^+$: 567.

EXAMPLE 37

9-{4-[4-(6-methoxy-pyridin-2-yl)-2,6-dimethyl-piperazin-1-yl]-butyl}-9H-fluorene-9-carboxylic acid-4-fluorobenzyl-amide.

Prepared analogously to Example 2 b from 1-(6-methoxy-pyridin-2-yl)-3,5-dimethyl-piperazine and 9-(4-bromo-butyl)-9H-fluorene-9-carboxylic acid-4-fluorobenzyl-amide.

Yield: 0.16 g (40.7% of theoretical).

Melting point: 78–79° C.

$C_{37}H_{41}FN_4O_2$ (M=592.76).

Calc.: molpeak (M-H): 591. Found: molpeak (M-H): 591.

EXAMPLE 38

9-{4-[4-(3-phenyl-[1,2,4]thiadiazol-5-yl)-piperazin-1-yl]-butyl}-9H-fluorene-9-carboxylic acid-(2,2,2-trifluoroethyl)-amide Prepared analogously to Example 2 b from 1-(3-phenyl-[1,2,4]thiadiazol-5-yl)-piperazine and 9-(4-bromo-butyl)-9H-fluorene-9-carboxylic acid-(2,2,2-trifluoroethyl)-amide.

Yield: 0.05 g (23.4% of theoretical).

Melting point: 115° C.

$C_{32}H_{32}F_3N_5OS$ (M=591.70).

| | | | | | |
|---|---|---|---|---|---|
| Calc: | C: 64.95 | H: 5.46 | N: 11.84 | S: 5.42 | F: 9.63 |
| Found: | C: 64.92 | H: 5.73 | N: 11.50 | S: 5.70 | F: 9.28 |

The following compounds may be prepared analogously to Examples 1 to 38:

(1) 9-{4-[4-(4'-fluoro-biphenyl-4-yl)-piperazin-1-yl]-butyl}-9H-fluorene-9-carboxylic acid-(2,2,2-trifluoroethyl)-amide (2) 9-{4-[4-(3'-fluoro-biphenyl-4-yl)-piperazin-1-yl]-butyl}-9H-fluorene-9-carboxylic acid-(2,2,2-trifluoroethyl)-amide (3) 9-{4-[4-(2'-fluoro-biphenyl-4-yl)-piperazin-1-yl]-butyl}-9H-fluorene-9-carboxylic acid-(2,2,2-trifluoroethyl)-amide (4) 9-{4-[4-(4'-chlorobiphenyl-4-yl)-piperazin-1-yl]-butyl}-9H-fluorene-9-carboxylic acid-(2,2,2-trifluoroethyl)-amide (5) 9-{4-[4-(3'-chlorobiphenyl-4-yl)-piperazin-1-yl]-butyl}-9H-fluorene-9-carboxylic acid-(2,2,2-trifluoroethyl)-amide (6) 9-{4-[4-(2'-chlorobiphenyl-4-yl)-piperazin-1-yl]-butyl}-9H-fluorene-9-carboxylic acid-(2,2,2-trifluoroethyl)-amide (7) 9-{4-[4-(4'-trifluoromethyl-biphenyl-4-yl)-piperazin-1-yl]-butyl}-9H-fluorene-9-carboxylic acid-(2,2,2-trifluoroethyl)-amide (8) 9-{4-[4-(3'-trifluoromethyl-biphenyl-4-yl)-piperazin-1-yl]-butyl}-9H-fluorene-9-carboxylic acid-(2,2,2-trifluoroethyl)-amide (9) 9-{4-[4-(2'-trifluoromethyl-biphenyl-4-yl)-piperazin-1-yl]-butyl}-9H-fluorene-9-carboxylic acid-(2,2,2-trifluoroethyl)-amide

(10) 9-{4-[4-(4'-methyl-biphenyl-4-yl)-piperazin-1-yl]-butyl}-9H-fluorene-9-carboxylic acid-(2,2,2-trifluoroethyl)-amide

(11) 9-{4-[4-(3'-methyl-biphenyl-4-yl)-piperazin-1-yl]-butyl}-9H-fluorene-9-carboxylic acid-(2,2,2-trifluoroethyl)-amide

(12) 9-{4-[4-(2'-methyl-biphenyl-4-yl)-piperazin-1-yl]-butyl}-9H-fluorene-9-carboxylic acid-(2,2,2-trifluoroethyl)-amide

(13) 9-{4-[4-(4'-methoxy-biphenyl-4-yl)-piperazin-1-yl]-butyl}-9H-fluorene-9-carboxylic acid-(2,2,2-trifluoroethyl)-amide

(14) 9-{4-[4-(3'-methoxy-biphenyl-4-yl)-piperazin-1-yl]-butyl}-9H-fluorene-9-carboxylic acid-(2,2,2-trifluoroethyl)-amide

(15) 9-{4-[4-(2'-methoxy-biphenyl-4-yl)-piperazin-1-yl]-butyl}-9H-fluorene-9-carboxylic acid-(2,2,2-trifluoroethyl)-amide

(16) 9-{4-[4-(4'-fluoro-biphenyl-3-yl)-piperazin-1-yl]-butyl}-9H-fluorene-9-carboxylic acid-(2,2,2-trifluoroethyl)-amide

(17) 9-{4-[4-(3'-fluoro-biphenyl-3-yl)-piperazin-1-yl]-butyl}-9H-fluorene-9-carboxylic acid-(2,2,2-trifluoroethyl)-amide

(18) 9-{4-[4-(2'-fluoro-biphenyl-3-yl)-piperazin-1-yl]-butyl}-9H-fluorene-9-carboxylic acid-(2,2,2-trifluoroethyl)-amide

(19) 9-{4-[4-(4'-chlorobiphenyl-3-yl)-piperazin-1-yl]-butyl}-9H-fluorene-9-carboxylic acid-(2,2,2-trifluoroethyl)-amide

(20) 9-{4-[4-(3'-chlorobiphenyl-3-yl)-piperazin-1-yl]-butyl}-9H-fluorene-9-carboxylic acid-(2,2,2-trifluoroethyl)-amide

(21) 9-{4-[4-(2'-chlorobiphenyl-3-yl)-piperazin-1-yl]-butyl}-9H-fluorene-9-carboxylic acid-(2,2,2-trifluoroethyl)-amide

(22) 9-{4-[4-(4'-trifluoromethyl-biphenyl-3-yl)-piperazin-1-yl]-butyl}-9H-fluorene-9-carboxylic acid-(2,2,2-trifluoroethyl)-amide

(23) 9-{4-[4-(3'-trifluoromethyl-biphenyl-3-yl)-piperazin-1-yl]-butyl}-9H-fluorene-9-carboxylic acid-(2,2,2-trifluoroethyl)-amide

(24) 9-{4-[4-(2'-trifluoromethyl-biphenyl-3-yl)-piperazin-1-yl]-butyl}-9H-fluorene-9-carboxylic acid-(2,2,2-trifluoroethyl)-amide

(25) 9-{4-[4-(4'-methyl-biphenyl-3-yl)-piperazin-1-yl]-butyl}-9H-fluorene-9-carboxylic acid-(2,2,2-trifluoroethyl)-amide

(26) 9-{4-[4-(3'-methyl-biphenyl-3-yl)-piperazin-1-yl]-butyl}-9H-fluorene-9-carboxylic acid-(2,2,2-trifluoroethyl)-amide

(27) 9-{4-[4-(2'-methyl-biphenyl-3-yl)-piperazin-1-yl]-butyl}-9H-fluorene-9-carboxylic acid-(2,2,2-trifluoroethyl)-amide

(28) 9-{4-[4-(4'-methoxy-biphenyl-3-yl)-piperazin-1-yl]-butyl}-9H-fluorene-9-carboxylic acid-(2,2,2-trifluoroethyl)-amide

(29) 9-{4-[4-(3'-methoxy-biphenyl-3-yl)-piperazin-1-yl]-butyl}-9H-fluorene-9-carboxylic acid-(2,2,2-trifluoroethyl)-amide

(30) 9-{4-[4-(2'-methoxy-biphenyl-3-yl)-piperazin-1-yl]-butyl}-9H-fluorene-9-carboxylic acid-(2,2,2-trifluoroethyl)-amide

(31) 9-{4-[4-(3-Thiazol-2-yl-phenyl)-piperazin-1-yl]-butyl}-9H-fluorene-9-carboxylic acid-(2,2,2-trifluoroethyl)-amide
(32) 9-{4-[4-(3-Thiophen-3-yl-phenyl)-piperazin-1-yl]-butyl}-9H-fluorene-9-carboxylic acid-(2,2,2-trifluoroethyl)-amide
(33) 9-(4-{4-[3-(1H-imidazol-4-yl)-phenyl]-piperazin-1-yl}-butyl)-9H-fluorene-9-carboxylic acid-(2,2,2-trifluoroethyl)-amide
(34) 9-(4-{4-[3-(1H-Pyrrol-2-yl)-phenyl]-piperazin-1-yl}-butyl)-9H-fluorene-9-carboxylic acid-(2,2,2-trifluoroethyl)-amide
(35) 9-{4-[4-(4-Thiazol-2-yl-phenyl)-piperazin-1-yl]-butyl}-9H-fluorene-9-carboxylic acid (2,2,2-trifluoroethyl)-amide
(36) 9-{4-[4-(4-Thiophen-3-yl-phenyl)-piperazin-1-yl]-butyl}-9H-fluorene-9-carboxylic acid-(2,2,2-trifluoroethyl)-amide
(37) 9-(4-{4-(4-(1H-imidazol-4-yl)-phenyl]-piperazin-1-yl}-butyl)-9H-fluorene-9-carboxylic acid-(2,2,2-trifluoroethyl)-amide
(38) 9-(4-{4-[4-(1H-Pyrrol-2-yl)-phenyl]-piperazin-1-yl}-butyl)-9H-fluorene-9-carboxylic acid-(2,2,2-trifluoroethyl)-amide
(39) 9-{4-[4-(4-Pyridin-2-yl-phenyl)-piperazin-1-yl]-butyl}-9H-fluorene-9-carboxylic acid-(2,2,2-trifluoroethyl)-amide
(40) 9-{4-[4-(6-phenyl-pyridin-2-yl)-piperazin-1-yl]-butyl}-9H-fluorene-9-carboxylic acid-(2,2,2-trifluoroethyl)-amide
(41) 9-{4-[4-(4-phenyl-pyrimidin-2-yl)-piperazin-1-yl]-butyl}-9H-fluorene-9-carboxylic acid-(2,2,2-trifluoroethyl)-amide
(42) 9-{4-[4-(2-phenyl-pyrimidin-5-yl)-piperazin-1-yl]-butyl}-9H-fluorene-9-carboxylic acid7 (2,2,2-trifluoroethyl)-amide
(43) 9-{4-[4-(5-phenyl-pyridin-2-yl)-piperazin-1-yl]-butyl}-9H-fluorene-9-carboxylic acid-(2,2,2-trifluoroethyl)-amide
(44) 9-{4-[4-(5-phenyl-thiophen-2-yl)-piperazin-1-yl]-butyl}-9H-fluorene-9-carboxylic acid-(2,2,2-trifluoroethyl)-amide
(45) 9-{4-[4-(5-phenyl-oxazol-2-yl)-piperazin-1-yl]-butyl}-9H-fluorene-9-carboxylic acid-(2,2,2-trifluoroethyl)-amide
(46) 9-[4-(4-[2,2']Bipyridinyl-6-yl-piperazin-1-yl)-butyl]-9H-fluorene-9-carboxylic acid-(2,2,2-trifluoroethyl)-amide
(47) 9-[4-(4-biphenyl-4-yl-piperazin-1-yl)-butyl]-9H-fluorene-9-carboxylic acid-methylamide
(48) 9-[4-(4-biphenyl-4-yl-piperazin-1-yl)-butyl]-9H-fluorene-9-carboxylic acid-ethylamide
(49) 9-[4-(4-biphenyl-4-yl-piperazin-1-yl)-butyl]-9H-fluorene-9-carboxylic acid-propylamide
(50) 9-[4-(4-biphenyl-4-yl-piperazin-1-yl)-butyl]-9H-fluorene-9-carboxylic acid-isopropylamide
(51) 9-[4-(4-biphenyl-4-yl-piperazin-1-yl)-butyl]-9H-fluorene-9-carboxylic acid-benzylamide
(52) 9-[4-(4-biphenyl-4-yl-piperazin-1-yl)-butyl]-9H-fluorene-9-carboxylic acid-phenylamide
(53) 9-[4-(4-biphenyl-4-yl-piperazin-1-yl)-butyl]-9H-fluorene-9-carboxylic acid-(pyridin-2-yl)-amide
(54) 9-[4-(4-biphenyl-4-yl-piperazin-1-yl)-butyl]-9H-fluorene-9-carboxylic acid-(4-fluorophenyl)-amide
(55) 9-[4-(4-biphenyl-4-yl-piperazin-1-yl)-butyl]-9H-fluorene-9-carboxylic acid-(3-chlorophenyl)-amide
(56) 9-[4-(4-biphenyl-4-yl-piperazin-1-yl)-butyl]-9H-fluorene-9-carboxylic acid-dimethylamide
(57) 9-[4-(4-biphenyl-4-yl-piperazin-1-yl)-butyl]-9H-fluorene-9-carboxylic acid-diethylamide
(58) {9-[4-(4-biphenyl-4-yl-piperazin-1-yl)-butyl]-9H-fluorene-9-yl}-aziridin-1-yl-methanone
(59) {9-[4-(4-biphenyl-4-yl-piperazin-1-yl)-butyl]-9H-fluorene-9-yl}-azetidin-1-yl-methanone
(60) {9-[4-(4-biphenyl-4-yl-piperazin-1-yl)-butyl]-9H-fluorene-9-yl}-pyrrolidin-1-yl-methanone
(61) {9-[4-(4-biphenyl-4-yl-piperazin-1-yl)-butyl]-9H-fluorene-9-yl}-piperidin-1-yl-methanone
(62) {9-[4-(4-biphenyl-4-yl-piperazin-1-yl)-butyl]-9H-fluorene-9-yl}-morpholin-1-yl-methanone
(63) 9-[4-(4-biphenyl-4-yl-piperazin-1-yl)-butyl]-2-fluoro-9H-fluorene-9-carboxylic acid-(2,2,2-trifluoroethyl)-amide
(64) 9-[4-(4-biphenyl-4-yl-piperazin-1-yl)-butyl]-2-methyl-9H-fluorene-9-carboxylic acid-(2,2,2-trifluoroethyl)-amide
(65) 9-[4-(4-biphenyl-4-yl-piperazin-1-yl)-butyl]-2-chloro-9H-fluorene-9-carboxylic acid-(2,2,2-trifluoroethyl)-amide
(66) 9-[4-(4-biphenyl-4-yl-piperazin-1-yl)-butyl]-3-methoxy-9H-fluorene-9-carboxylic acid-(2,2,2-trifluoroethyl)-amide
(67) 9-[4-(4-biphenyl-3-yl-piperazin-1-yl)-butyl]-2-fluoro-9H-fluorene-9-carboxylic acid-(2,2,2-trifluoroethyl)-amide
(68) 9-[4-(4-biphenyl-3-yl-piperazin-1-yl)-butyl]-2-methyl-9H-fluorene-9-carboxylic acid-(2,2,2-trifluoroethyl)-amide
(69) 9-[4-(4-biphenyl-3-yl-piperazin-1-yl)-butyl]-2-chloro-9H-fluorene-9-carboxylic acid-(2,2,2-trifluoroethyl)-amide
(70) 9-[4-(4-biphenyl-3-yl-piperazin-1-yl)-butyl]-3-methoxy-9H-fluorene-9-carboxylic acid-(2,2,2-trifluoroethyl)-amide
(71) 9-[3-(4-biphenyl-4-yl-piperazin-1-yl)-propyl]-9H-fluorene-9-carboxylic acid-(2,2,2-trifluoroethyl)-amide
(72) 9-[3-(4-biphenyl-3-yl-piperazin-1-yl)-propyl]-9H-fluorene-9-carboxylic acid-(2,2,2-trifluoroethyl)-amide
(73) 9-{4-[4-(6-methoxy-pyridin-2-yl)-2-(R,S)-methyl-piperazin-1-yl]-butyl}-9H-fluorene-9-carboxylic acid-(2,2,2-trifluoroethyl)-amide
(74) 9-{4-[4-(5-trifluoromethyl-pyridin-2-yl)-[1,4]diazepan-1-yl]-butyl}-9-H-fluorene-9-carboxylic acid-(2,2,2-trifluoroethyl)-amide
(75) 9-(5-{4-[6-(pyridin-3-yloxy)-pyridin-2-yl]-piperazin-1-yl}-pentyl)-9H-fluorene-9-carboxylic acid-(2,2,2-trifluoroethyl)-amide

EXAMPLE 40

Tablets Containing 5 mg of Active Substance Per Tablet

Composition:

| | |
|---|---|
| active substance | 5.0 mg |
| lactose monohydrate | 70.8 mg |
| microcrystalline cellulose | 40.0 mg |
| sodium carboxymethylcellulose, insolubly crosslinked | 3.0 mg |
| magnesium stearate | 1.2 mg |

Preparation:

The active substance is mixed for 15 minutes with lactose monohydrate, microcrystalline cellulose and sodium carboxymethylcellulose in a suitable diffusion mixer. Magnesium stearate is added and mixed with the other substances for another 3 minutes.

The finished mixture is compressed in a tablet press to form facetted flat round tablets.

Diameter of the tablet: 7 mm

Weight of a tablet: 120 mg

EXAMPLE 41

Capsules Containing 50 mg of Active Substance Per Capsule

Composition:

| | |
|---|---|
| active substance | 50.0 mg |
| lactose monohydrate | 130.0 mg |
| corn starch | 65.0 mg |
| highly dispersed silicon dioxide | 2.5 mg |
| magnesium stearate | 2.5 mg |

Preparation:

A starch paste is prepared by swelling some of the corn starch in a suitable amount of hot water. The paste is then left to cool to room temperature.

The active substance is premixed for 15 minutes in a suitable mixer with lactose monohydrate and corn starch. The starch paste is added and the mixture is mixed with sufficient water to produce a moist homogeneous mass. The moist mass is passed through a screen with a mesh size of 1.6 mm. The screened granules are dried on racks at about 55° C. for 12 hours.

The dried granules are then passed through screens with mesh sizes of 1.2 and 0.8 mm. Highly dispersed silica is mixed with the granules in a suitable mixer for 3 minutes. Then magnesium stearate is added and mixing is continued for another 3 minutes.

The finished mixture is packed into empty size 1 hard gelatine capsule shells using a capsule filling machine.

EXAMPLE 42

Tablets Containing 200 mg of Active Substance Per Tablet

Composition:

| | |
|---|---|
| active substance | 200.0 mg |
| lactose-monohydrate | 167.0 mg |
| microcrystalline cellulose | 80.0 mg |
| hydroxypropyl-methylcellulose, type 2910 | 10.0 mg |
| poly-1-vinyl-2-pyrrolidone, insolubly crosslinked | 20.0 mg |
| magnesium stearate | 3.0 mg |

Preparation:

HPMC is dispersed in hot water. After cooling, the mixture yields a clear solution.

The active substance is premixed in a suitable mixer for 5 minutes with lactose monohydrate and microcrystalline cellulose. The HPMC solution is added and the mixing is continued until a homogeneous moist composition is obtained. The moist composition is passed through a screen with a mesh size of 1.6 mm. The screened granules are dried on racks at about 55° C. for 12 hours.

The dried granules are then passed through screens with mesh sizes of 1.2 and 0.8 mm. Poly-1-vinyl-2-pyrrolidone is mixed with the granules in a suitable mixer for 3 minutes. Then magnesium stearate is added and mixing is continued for another 3 minutes.

The finished mixture is compressed in a tablet press to form oblong tablets (16.2×7.9 mm).

Weight of a tablet: 480 mg

What is claimed is:

1. A compound of the formula (I)

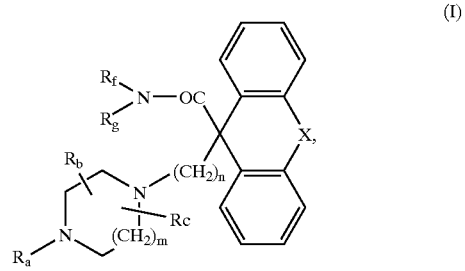

wherein n denotes the number 1, 2, 3, 4 or 5, m denotes the number 2,

X denotes a carbon-carbon bond, $R_a$ denotes a phenyl group or a heteroaryl group chosen from pyridinyl, pyrimidinyl, thiophenyl, oxazolyl and 1, 2, 4 thiadiazolyl each substituted by the groups $R_1$ and $R_2$, wherein $R_1$ denotes a hydrogen, fluorine, chlorine, a $C_{1-3}$-alkyl group wherein the hydrogen atoms of the alkyl are optionally wholly or partly replaced by fluorine atoms, a $C_{1-4}$-alkoxy group, a phenoxy, phenyl-$C_{1-3}$-alkoxy, nitro or amino, wherein the abovementioned phenyl of the phenoxy is optionally substituted by chlorine or methoxy, and $R_2$ denotes a hydrogen, chlorine or $C_{1-4}$-alkoxy, or $R_a$ denotes a heteroaryl chosen from pyridinyl, pyrimidinyl thiophenyl, oxazolyl and 1, 2, 4 thiadiazolyl or phenyl group which is substituted in each case by a phenyl group, $R_b$ and $R_c$ independently of one another denote a hydrogen atom or a $C_{1-3}$-alkyl group and $R_f$ denotes $C_{1-6}$-alkyl wherein the hydrogen atoms of the alkyl are optionally wholly or partly replaced by fluorine atoms, phenyl-$C_{1-3}$-alkyl wherein the phenyl is optionally substituted by fluorine or $C_{1-3}$-alkoxy, $R_g$ is hydrogen;

or the enantiomeres, diastereomers or the salts thereof.

2. The compound according to claim 1, wherein n denotes the number 3, 4 or 5.

3. The compound according to claim 1, wherein $R_b$ and $R_c$ independently of one another denote a hydrogen atom or a methyl group.

4. The compound according to claim 1, wherein n denotes the number 4, m denotes the number 2.

5. A compound chosen from

9-[4-(4-biphenyl-3-yl-piperazin-1-yl)-butyl]-9H-fluorene-9-carboxylic acid-(2,2,2-trifluoroethyl)-amide and 9-[4-(4-biphenyl-4-yl-piperazin-1-yl)-butyl]-9H-fluorene-9-carboxylic acid-(2,2,2-trifluoroethyl)-amide or the enantiomeres, diastereomers or the salts thereof.

6. A physiologically acceptable salt of the compound according to claim 1.

7. A pharmaceutical composition comprising a pharmaceutically effective amount of a compound according to claim 1 with one or more pharmaceutically acceptable inert carriers and/or diluents.

8. A method of treating a disease selected from hyperlipidaemias, atherosclerosis, diabetes mellitus, adiposity and pancreatitis, said method comprising administering to a patient in need thereof a pharmaceutically effective amount of a compound according to claim 1.

9. The method according to claim 8 wherein the compound is combined with another lipid-lowering agent.

10. Process for preparing a compound of the formula (I) according to claim 1, comprising a) reacting under suitable conditions a compound of formula

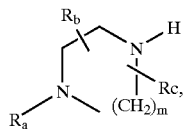

(II)

wherein $R_a$, $R_b$ and $R_c$ are defined as in claim 1, with a compound of formula

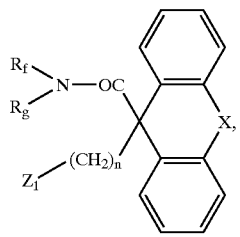

(III)

wherein n, $R_f$, $R_g$ and the tricyclic system are defined as in claim 1 and $Z_1$ denotes a nucleofugic leaving group, or b) reacting under suitable conditions a compound of formula

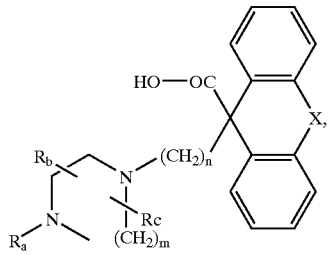

(IV)

with an amine of formula

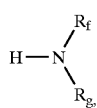

(V)

wherein $R_f$ and $R_g$ are defined as in claim 1, or with the reactive derivatives thereof and c) optionally reducing under suitable conditions the product of a) or b) which contains a nitro group if desired into a corresponding amino compound and/or d) if $R_f$ denotes a hydrogen atom alkylating under suitable conditions the product into a corresponding compound wherein $R_f$ denotes a phenyl-$C_{1-3}$-alkyl group, and/or e) cleaving under suitable conditions any protecting group using to protect reactive groups during the reactions and/or resolving the product any of the product above into its stereoisomers and/or converting any of the products above into the physiologically acceptable salts thereof.

* * * * *